United States Patent [19]

Morgan

[11] 4,135,047

[45] Jan. 16, 1979

[54] PREPARATION OF THIOETHERS USING A BENZOPINACOL INITIATOR

[75] Inventor: Charles R. Morgan, Brookeville, Md.

[73] Assignee: W. R. Grace & Co., New York, N.Y.

[21] Appl. No.: 889,794

[22] Filed: Mar. 23, 1978

Related U.S. Application Data

[63] Continuation-in-part of Ser. No. 790,796, Apr. 25, 1977, abandoned, which is a continuation-in-part of Ser. No. 651,365, Jan. 22, 1976, Pat. No. 4,020,233.

[51] Int. Cl.$^2$ .................. C07D 251/30; C07C 53/22; C07C 149/18; C07C 149/20
[52] U.S. Cl. .................. 544/219; 560/152; 560/125; 260/609 B; 562/512
[58] Field of Search .................. 260/526 S, 609 B; 560/152, 125; 544/219

[56] References Cited

U.S. PATENT DOCUMENTS 3,637,419  1/1972  Lundsager .................. 117/93.31
3,662,023  5/1972  Kehr et al. .................. 260/858

Primary Examiner—John M. Ford
Attorney, Agent, or Firm—Richard P. Plunkett; William W. McDowell, Jr.

[57] ABSTRACT

This invention relates to a process for preparing thioethers by the addition of an SH group from a thiol-containing compound, e.g., an alcohol, ester or acid, across at least one double bond of an ethylenically unsaturated compound in the presence of an initiator comprising a pinacol of the general formula:

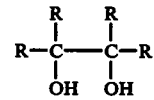

wherein R is phenyl or substituted phenyl, said substituents being members of the group consisting of halogen, alkyloxy and alkyl, said alkyloxy and alkyl containing 1 to 6 carbon atoms.

4 Claims, No Drawings

PREPARATION OF THIOETHERS USING A BENZOPINACOL INITIATOR

This application is a continuation-in-part of my co-pending application having Ser. No. 790,796, filed Apr. 25, 1977, now abandoned, which in turn is a continuation-in-part of my application having Ser. No. 651,365, filed Jan. 22, 1976, now U.S. Pat. No. 4,020,233.

This invention relates to a process for preparing thioethers by the addition of a thiol-containing compound, e. g., an alcohol, ester or acid, to ethylenically unsaturated compounds in the presence of a pinacol initiator.

Accordingly, this invention relates to a process for preparing thioethers by the addition of an SH group from a thiol-containing compound of the formula $R_1(CH_2)_nSH$ wherein n is 1 to 6; $R_1$ is a member of the group consisting of

and $R_2$ is an alkyl containing 1 to 6 carbon atoms with the proviso that, when $R_1$ is -OH, n is 2 to 6 across at least one double bond $>C=C<$ of an ethylenically unsaturated compound under normal processing conditions involving only atmospheric pressure in the presence of an initiator comprising a pinacol of the general formula:

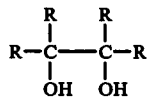

wherein R is phenyl or substituted phenyl, said substituents being members of the group consisting of halogen, alkyloxy and alkyl, said alkyloxy and alkyl containing 1 to 6 carbon atoms at a temperature of at least 50° C, preferably 80–150° C.

Examples of thiol-containing compounds operable herein include, but are not limited to, hexyl mercaptoacetate, methyl mercaptoacetate, methyl 7-mercaptoheptanoate, propy; 7-mercaptoheptanoate, thioethanol, 6-mercaptohexyl alcohol, 3-mercapto n-propyl alcohol, thioglycolic acid, 7-mercaptoheptanoic acid and 4-mercaptobutyric acid.

The resultant thioether, depending on whether the thiol-containing compound is an alcohol, ester or acid, have various uses. That is, the hydroxy terminated thioether can be esterified with an unsaturated acid, e. g., acrylic acid, to form an acrylate. The acid terminated thioether can be reacted with an unsaturated alcohol, e. g., allyl alcohol, to form an olefinic esterthio compound. The ester terminated thioether can be hydrolyzed to an acid or reduced to an alcohol. Additionally, using any of the thiol-containing compounds as a reactant, an ethylenically unsaturated thioether can be formed if the ethylenically unsaturated compound contains two or more carbon-to-carbon double bonds which are present in a stoichiometric excess in relation to the thiol in the thiol-containing compound. See, for example, U.S. Pat. No. 3,784,524.

As used herein, the term "ethylenically unsaturated compound" includes compounds having terminal, internal or pendant ethylenic unsaturation or any combination thereof. Any ethylenically unsaturated compound as herein defined including those containing more than one carbon-to-carbon double bond is operable in the instant invention to form thioethers. In addition, other functional groups such as esters, ethers, ketones, halides, amides and hydroxyls can also be present in the ethylenically unsaturated compound without interfering with or taking part in the reaction set forth herein. The hydrocarbon moieties of these compounds may be straight-chained or branched, aromatic, aliphatic or cycloaliphatic.

The thiol-containing compound in the mixture is reacted with the desired ethylenically unsaturated compound in the presence of a pinacol at slightly elevated temperatures, i. e., at least 50° C, preferably 80°–150° C, to form the corresponding thioether. The resultant product, if necessary, is purified by distillation or crystallization, which methods are well known to one skilled in the art.

The reaction of the instant invention is initiated by a pinacol of the general formula:

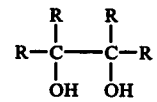

wherein R is phenyl or substituted phenyl, said substituents being members of the group consisting of halogen, alkyloxy and alkyl, said alkyloxy and alkyl containing 1 to 6 carbon atoms.

The preferred pinacol used herein is benzopinacol because of its commercial availability and ease of synthesis. However, other pinacols are equally operable to initiate the reaction.

Examples of these pinacols include, but are not limited to, 4,4'-dichlorobenzopinacol, 4,4'-dibromobenzopinacol, 4,4'-diiodobenzopinacol, 4,4',4'',4'''-tetrachlorobenzopinacol, 2,4-2',4'-tetrachlorobenzopinacol, 4,4'-dimethylbenzopinacol, 3,3'-dimethylbenzopinacol, 2,2'-dimethylbenzopinacol, 3,4-3',4'-tetramethylbenzopinacol, 4,4'-dimethoxybenzopinacol, 4,4',4'',4'''-tetramethoxybenzopinacol, and 4,4'-dichloro-4'',4'''-dimethylbenzopinacol.

The pinacol is added to the composition in amounts ranging from 0.01-5% preferably 0.1-3% by weight based on the combined weights of the ethylenically unsaturated compound and the thiol-containing compound.

The thiol-containing compound is added to the reaction in an amount ranging from that sufficient to react with one up to all the carbon-to-carbon double bonds in the ethylenically unsaturated compound. Thus, the thiol-containing reactants herein can be reacted with monoenes, dienes, trienes, tetraenes and the like in an amount sufficient to satisfy at least one, a portion of, or all the carbon-to-carbon double bonds present in the ethylenically unsaturated compound.

If desired, the reaction can be carried out in a solvent. Operable solvents should be free of reactive ethylenic unsaturation and have a boiling point higher than the reaction temperature. Such solvents include, but are not limited to, aromatic hydrocarbons, e. g., benzene, toluene, xylene and saturated hydrocarbons such as hexane, cyclohexane, heptane and the like.

Carrying out the instant invention, the preferred method of operation is to add the benzopinacol initiator to the thiol-containing compound which is then added to the ethylenically unsaturated compound which may have been preheated to the desired reaction temperature, either alone or admixed with a solvent. Heating is continued until the corresponding thioether is formed.

The following examples will aid to explain, but specifically not limit, the instant invention. Unless otherwise noted, all parts and percentages are by weight.

EXAMPLE 1

1 g of commercially available benzopinacol was dissolved in 50 g of commercially available triallyl cyanurate (11.48 mmoles C=C/g). 51.7 g of methyl-3-mercapto propionate (8.16 meq.SH/g) and 0.02 g of phosphorous acid were added to the solution. After mixing at 25° C the mixture contained 4.15 meq. SH/g (theory 4.18 meq. SH/g). The mixture was heated with stirring to 110° C whereat the mixture exothermed to 195° C. The thiol content of the resultant product containing mixture was 0.25 meq. SH/g showing addition of SH to the olefinic double bond.

EXAMPLE 2

40 g of commercially available 1-dodecene (5.88 mmoles C=C/g) was mixed with 28.87 g of methyl-3-mercaptopropionate (8.16 meq. SH/g) in which 1.38 g of benzopinacol was dissolved at 25° C. The mixture thus obtained has a calculated SH of 3.42 meq./g. The mixture was heated within 15 minutes to 87–90° C when it exothermed to about 160° C. The mixture was allowed to cool to 125° C whereat it was heated for 3 hours. The reacted mixture was analyzed and found to have an SH of 0.76 meq./g showing addition of SH to the olefinic double bond.

EXAMPLE 3

40 g of commercially available 1-dodecene (5.88 mmoles C=C/g) was mixed with 28.87 g of methyl-3-mercaptopropionate (8.16 meq. SH/g) to which was added 1.38 g of benzopinacol and 0.014 g phosphorous acid at 25° C. The mixture thus obtained has a calculated SH of 3.41 meq./g. The mixture was heated to about 85° C where it exothermed to 150° C. The reaction was continued for ½ hour at 100° C. On analysis, the reaction mixture was found to have an SH of 0.64 meq./g showing addition of SH to the olefinic double bond.

EXAMPLE 4

23.48 g of 2-mercaptoethanol (12.54 meq. SH/g) were charged to a 200 ml. round bottom flask equipped with thermometer, reflux condenser and stirrer along with 50.0 g commercially available 1-dodecene (5.89 mmoles C=C/g) and 1.47 g benzopinacol. The reactants were heated at 125° C with stirring for 3 hours. The reacted mixture on analysis was found to have an SH of 0.25 meq./g showing addition of SH to the olefinic double bond.

EXAMPLE 5

31.43 g of 3-mercaptopropionic acid (9.37 meq. SH/g) were charged to a 200 ml. round bottom flask equipped with thermometer, reflux condenser and stirrer along with 50.0 g commercially available 1-dodecene (5.89 mmoles C=C/g) and 1.63 g benzopinacol. The reaction exothermed to 41° C upon the addition of the benzopinacol. The reactants were heated at 125° C with stirring for 3 hours. The reacted mixture on analysis was found to have an SH of 0.42 meq./g showing addition of SH to the olefinic double bond.

EXAMPLE 6

40 g of commercially available cyclohexene (8.33 mmoles C=C/g), 40.85 g methyl-3-mercaptopropionate (8.16 meq SH/g) and 1.62 g benzopinacol were charged to a 200 ml 3 neck flask equipped with stirrer, thermometer and reflux condenser at 25° C. The resulting mixture had an SH value of 3.87 meq/g. The mixture was heated to refluxing (89° C) and refluxed for 1 hours with the temperature slowly rising to 100° C after 1 hour for a short period. The resultant product mixture on analysis had an SH value of 2.09 meq/g indicative of the addition of SH to the internal double bond.

EXAMPLE 7

40 g of commercially available 1-dodecene (5.88 mmoles C=C/g was mixed with 28.87 g of methyl-3-mercaptopropionate (8.16 meq. SH/g) in which 1.38 g of 4,4'-dichlorobenzopinacol was dissolved at 35° C. The mixture thus obtained has a calculated SH of 3.42 meq./g. The mixture was heated within 15 minutes to 88–93° C when it exothermed to about 141° C. The mixture was allowed to cool to 125° C whereat it was heated for 3 hours. The reacted mixture was analyzed and found to have an SH of 0.12 meq./g showing addition of SH to the olefinic double bond.

What is claimed is:

1. The process of forming a thioether which comprises reacting a thiol-containing compound of the formula: $R_1(CH_2)_nSH$, wherein n is 1 to 6; $R_1$ is a member of the group consisting of

and $R_2$ is an alkyl containing 1 to 6 carbon atoms with the proviso that, when $R_1$ is —OH, n is 2 to 6, across the double bond of an ethylenically unsaturated compound in the presence of an initiator comprising a pinacol of the formula:

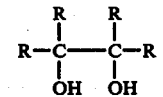

wherein R is phenyl or substituted phenyl, said substituents being members of the group consisting of halogen, alkyloxy and alkyl, said alkyloxy and alkyl containing 1 to 6 carbon atoms.

2. The process according to claim 1 wherein the reaction was carried out at a temperature in the range 50–150° C.

3. The process according to claim 1 wherein the initiator is benzopinacol.

4. The process according to claim 1 wherein the initiator is added in an amount ranging from 0.01–5.0% based on the weight of the ethylenically unsaturated compound and the thiol-containing compound.

* * * * *